(12) United States Patent
Maris

(10) Patent No.: US 6,381,019 B1
(45) Date of Patent: Apr. 30, 2002

(54) ULTRASONIC GENERATOR AND DETECTOR USING AN OPTICAL MASK HAVING A GRATING FOR LAUNCHING A PLURALITY OF SPATIALLY DISTRIBUTED, TIME VARYING STRAIN PULSES IN A SAMPLE

(75) Inventor: Humphrey J. Maris, Barrington, RI (US)

(73) Assignee: Brown University Research Foundation, Providence, RI (US)

( * ) Notice: Subject to any disclaimer, the term of this patent is extended or adjusted under 35 U.S.C. 154(b) by 0 days.

(21) Appl. No.: 09/608,865

(22) Filed: Jun. 30, 2000

(51) Int. Cl.[7] .............................................. G01N 21/00
(52) U.S. Cl. ...................... 356/432; 356/445; 356/630; 73/800; 374/5
(58) Field of Search .......................... 356/32, 432, 445, 356/446, 448, 433–440, 630–632; 73/655, 760, 800, 643; 374/5, 7, 17, 57

(56) References Cited

U.S. PATENT DOCUMENTS

| | | | | |
|---|---|---|---|---|
| 4,632,561 A | * | 12/1986 | Rosencwaig et al. | 356/432 |
| 4,652,757 A | * | 3/1987 | Carver | 250/360.1 |
| 4,710,030 A | | 12/1987 | Tauc et al. | 356/432 |
| 5,633,711 A | * | 5/1997 | Nelson et al. | 356/318 |
| 5,706,094 A | | 1/1998 | Maris | 356/432 |
| 5,748,317 A | | 5/1998 | Maris et al. | 356/357 |
| 5,748,318 A | | 5/1998 | Maris et al. | 356/381 |
| 5,844,684 A | | 12/1998 | Maris et al. | 356/432 |
| 5,864,393 A | | 1/1999 | Maris | 356/28 |
| 5,959,735 A | | 9/1999 | Maris et al. | 356/381 |
| 6,008,906 A | | 12/1999 | Maris | 356/432 |
| 6,025,918 A | | 2/2000 | Maris | 356/388 |
| 6,038,026 A | | 3/2000 | Maris | 356/357 |
| 6,175,416 B1 | * | 1/2001 | Maris et al. | 356/381 |
| 6,188,478 B1 | * | 2/2001 | Fuchs et al. | 356/432 |
| 6,211,961 B1 | * | 4/2001 | Maris | 356/432 |

* cited by examiner

Primary Examiner—Hoa Q. Pham
(74) Attorney, Agent, or Firm—Harrington & Smith, LLP

(57) ABSTRACT

A method and a system are disclosed for determining at least one characteristic of a sample that contains a substrate and at least one film disposed on or over a surface of the substrate. The method includes a first step of placing a mask over a free surface of the at least one film, where the mask has a top surface and a bottom surface that is placed adjacent to the free surface of the film. The bottom surface of the mask has formed therein or thereon a plurality of features for forming at least one grating. A next step directs optical pump pulses through the mask to the free surface of the film, where individual ones of the pump pulses are followed by at least one optical probe pulse. The pump pulses are spatially distributed by the grating for launching a plurality of spatially distributed, time varying strain pulses within the film, which cause a detectable change in optical constants of the film. A next step detects a reflected or a transmitted portion of the probe pulses, which are also spatially distributed by the grating. A next step measures a change in at least one characteristic of at least one of reflected or transmitted probe pulses due to the change in optical constants, and a further step determines the at least one characteristic of the sample from the measured change in the at least one characteristic of the probe pulses. An optical mask is also disclosed herein, and forms a part of these teachings.

52 Claims, 5 Drawing Sheets

ULTRASONIC GENERATOR AND DETECTOR USING AN OPTICAL MASK HAVING A GRATING FOR LAUNCHING A PLURALITY OF SPATIALLY DISTRIBUTED, TIME VARYING STRAIN PULSES IN A SAMPLE

STATEMENT OF GOVERNMENT RIGHTS

This invention was made with government support under grant number DOE DE-FG02-86ER45267, awarded by the Department of Energy. The government has certain rights in the invention.

FIELD OF THE INVENTION

This invention relates generally to non-destructive material analysis and characterization systems and methods and, more particularly, relates to optically based materials analysis and characterization systems that employ light pulses of picosecond and sub-picosecond duration to generate a localized stress in a sample that results in propagating strain waves, and that detect changes in optical constants of the sample material due to the propagating strain waves.

BACKGROUND OF THE INVENTION

A number of U.S. Patents exist in the general area of picosecond ultrasonics. In most of these U.S. Patents a pump light pulse is directed at the surface of a sample. The pump light pulse raises the temperature of a layer near the surface of the sample and sets up a stress in this region. A time-varying strain is then generated in the sample. The strain is detected by means of a probe light pulse applied to the sample at a later time. Hereinafter this approach will be referred to as the "standard method". From the arrival time, amplitude, and shape of the detected signals, a data processor is enabled to determine a number of characteristics of the sample. These characteristics include, but are not limited to, the film thickness, the adhesion between a film and the substrate, the adhesion between one film and another film, the orientation of crystalline grains making up a film, the size of grains, the crystal phase of a film, the electrical resistivity of a film, the rate of electromigration within a film, and the yield stress of a film.

In some of these U.S. Patents measurements can be made by means of a second method, referred to herein for convenience as a "grating method". In this approach, the pump light is divided into two beams that are directed onto the sample surface at oblique angles. Because of the constructive and destructive interference between the two beams, the intensity of the pump light varies periodically across the sample surface. Thus, the temperature rise of the sample surface and the induced stress will also vary periodically across the sample surface. This stress launches a strain disturbance into the sample that varies periodically across the sample surface. This strain field causes the optical constants of the sample, and the displacement of the sample surface, to vary across the sample surface and, as a consequence, when a probe pulse is incident onto the surface a fraction of the probe pulse will be diffracted, rather than undergoing specular reflection. Thus, the strain field acts as a diffraction grating. By a measurement of the intensity of the diffracted probe light as a function of the time after the application of the pump light pulse, the propagation of strain in the sample can be investigated, and physical properties of the sample determined. The grating method can also be used to determine the various sample properties that were listed above.

These two methods each have some limitations. For example, in the standard method, in order to determine the thickness of a film the sound velocity in the film must be known. This value can be taken from measurements made on a bulk sample of the same material composition as the film. In some cases, it is also possible to estimate the sound velocity from a measurement of the reflection coefficient of the strain pulse at the interface between one film and another. This measurement enables a comparison of the acoustic impedances of the two films to be made.

The grating method also exhibits a number of limitations. For example, it is necessary to build the apparatus in a way that ensures that the phase relation between the two pump beams remains constant. In addition, the diffracted component of the probe light may have a low intensity and thus may be difficult to measure accurately in the presence of light diffusely scattered from the surface of the sample.

Based on the foregoing, it can be appreciated that a need exists to provide an improved approach to ultrasonic sample characterization that overcomes the foregoing and other problems.

OBJECTS AND ADVANTAGES

It is a first object and advantage of these teachings to provide an improved sample characterization system and method that overcomes the foregoing an other problems.

It is another object and advantage of these teachings to provide an improved sample characterization system and method that employs an optical mask.

SUMMARY OF THE INVENTION

The foregoing and other problems are overcome and the objects of the invention are realized by methods and apparatus in accordance with embodiments of this invention.

An improved method and apparatus in accordance with these teachings generates and detects strain pulses in a sample, while retaining many of the advantages of the standard method, while at the same time making it possible to determine the sound velocity in the sample. A transparent plate, referred to herein for convenience as a mask, is placed over the sample. The bottom of the plate has a periodic grating etched into its surface. A pump light pulse is directed through the transparent mask onto the sample. The periodic grating of the mask distorts the wavefront of the light pulse and, as a result, the intensity of the light incident onto the film varies periodically with position across the sample surface. This results in a heating of the film surface that varies periodically with position. The regions of the film that are heated expand and, as a result, spatially distributed strain pulses (disturbances) are launched into the sample. The strain pulses result in a change in the optical constants of the sample, and this change is detected by means of a time-delayed probe pulse also directed onto the sample through the transparent mask. As in the standard method and the grating method, the improved method in accordance with the teachings herein can be used to determine various characteristics of the sample. These characteristics include, but need not be limited to, the film thickness, the adhesion between a film and the substrate, the adhesion between one film and another film, the orientation of crystalline grains making up a film, the size of grains, the crystal phase of a film, the electrical resistivity of a film, the rate of electromigration within a film, and the yield stress of a film.

In one preferred embodiment, the pump and probe beams are directed through the mask at normal incidence. The probe is delayed relative to the pump by means of a variable optical path provided by a movable stage. The change in the intensity of the reflected probe beam is measured as a function of the time delay between the application of the pump and probe pulses. To improve the signal to noise ratio the intensity of the pulses composing the pump beam is modulated at frequency f by means of an acousto-optic modulator. The output of the detector of the reflected probe beam is fed into a lock-in amplifier for which the reference signal is at the same frequency f. The measured change $\Delta R(t)$ in reflectivity of the sample is compared with the results of a simulated reflectivity change $\Delta R_{sim}(t)$. The change $\Delta R_{sim}(t)$ can be determined as follows: A) An initial estimate is made for the parameters of the sample. These parameters include, but are not necessarily limited to, the thickness, density, sound velocity, thermal expansion, specific heat, and optical constants of the different films, the adhesion between the films, the orientation of crystalline grains making up a film, the size of grains, the crystal phase and electrical resistivity of each film. B) Based on these assumed values, the stress in the structure that is induced by the pump light pulse is calculated. C) The time-dependent strain in the sample is then calculated. D) From this strain, the expected change in reflectivity $\Delta R_{sim}(t)$ is found. E) This change is compared with the measured reflectivity $\Delta R(t)$. The parameters of the sample are then adjusted and the procedure repeated in order to achieve the best possible agreement between $\Delta R(t)$ and $\Delta R_{sim}(t)$.

A method and a system are thus disclosed for determining at least one characteristic of a sample containing a substrate and at least one film disposed on or over a surface of the substrate. The method includes a first step of placing a mask over a free surface of the at least one film, where the mask has a top surface and a bottom surface that is placed adjacent to the free surface of the film. The bottom surface of the mask has formed therein or thereon a plurality of features for forming at least one grating. A next step directs optical pump pulses through the mask to the free surface of the film, where individual ones of the pump pulses are followed by at least one optical probe pulse.

In accordance with an aspect of these teachings the pump pulses are spatially distributed by the grating for launching a plurality of spatially distributed, time varying strain pulses within the film. The strain pulses cause a detectable change in optical constants of the film.

A next step detects a reflected or a transmitted portion of the probe pulses, which are also spatially distributed by the grating.

A next step of the method measures a change in at least one characteristic of at least one of reflected or transmitted probe pulses due to the change in optical constants, and a further step determines the at least one characteristic of the sample from the measured change in the at least one characteristic of the probe pulses.

In addition to changes in reflectivity arising from the strain pulses that are launched in the sample, there may be components that arise from a spatial variation in temperature, and/or from a spatial variation in a density of electrons and holes in the sample.

For example, the sample may include at least one region that is implanted during an ion implant process and, using the spatially varying density of electrons and holes in the film, a determined characteristic of the sample can be related to at least one of (A) a number of ions implanted per unit area of the surface of the sample; (B) a kinetic energy of the ions that are directed at the surface of the sample; (C) a direction at which the ion beam is incident onto the surface of the sample; (D) an ion current per unit area during the ion implant process; (E) the species of the implanted ion; (F) the charge on the implanted ion; (G) a duration of time that the ion-implanted sample is annealed; and (H) a temperature at which the ion-implanted sample is annealed.

An optical mask is also disclosed herein, and forms a part of these teachings.

Also disclosed is a method for determining the electrical resistivity of a film that comprises part of a sample having an underlying substrate. The method includes steps of: (A) placing a mask over a free surface of the film, the mask having a top surface and a bottom surface that is placed adjacent to the free surface of the film, the bottom surface of the mask comprising a plurality of features having a known feature repeat distance w; (B) directing optical pump pulses through the mask to the free surface of the film, individual ones of the pump pulses being followed by at least one optical probe pulse, said pump pulses being spatially distributed by said at least one grating for generating a spatially distributed temperature variation within the film that causes a change in optical constants of the film; (C) detecting a reflected or transmitted portion of said probe pulses, said probe pulses also being spatially distributed by said at least one grating; (D) measuring $\Delta R(t)$ as a function of the time t after the application of the pump pulses using the mask of known repeat distance w; (E) assuming values for the thermal conductivity $\kappa_{film}$ of the film, the thermal conductivity $\kappa_{sub}$ of the substrate, and the Kapitza conductance $\sigma_K$ between the film and the substrate; (F) calculating an initial temperature distribution within the film; (G) calculating the temperature distribution within the film at later times based on the assumed values for the thermal conductivity of the film, the thermal conductivity of the substrate, and the Kapitza conductance between the film and the substrate; (H) calculating an expected change in reflectivity $\Delta R(t)$ based on the calculated temperature distribution; (I) adjusting the parameters $\kappa_{film}$, $\kappa_{sub}$, and $\sigma_K$, and repeating Steps (F)–(H) so as to obtain a best fit to the measured $\Delta R(t)$; and calculating the electrical resistivity from the thermal conductivity.

BRIEF DESCRIPTION OF THE DRAWINGS

The above set forth and other features of the invention are made more apparent in the ensuing Detailed Description of the Invention when read in conjunction with the attached Drawings, wherein.

DETAILED DESCRIPTION OF THE INVENTION

Figure 1:
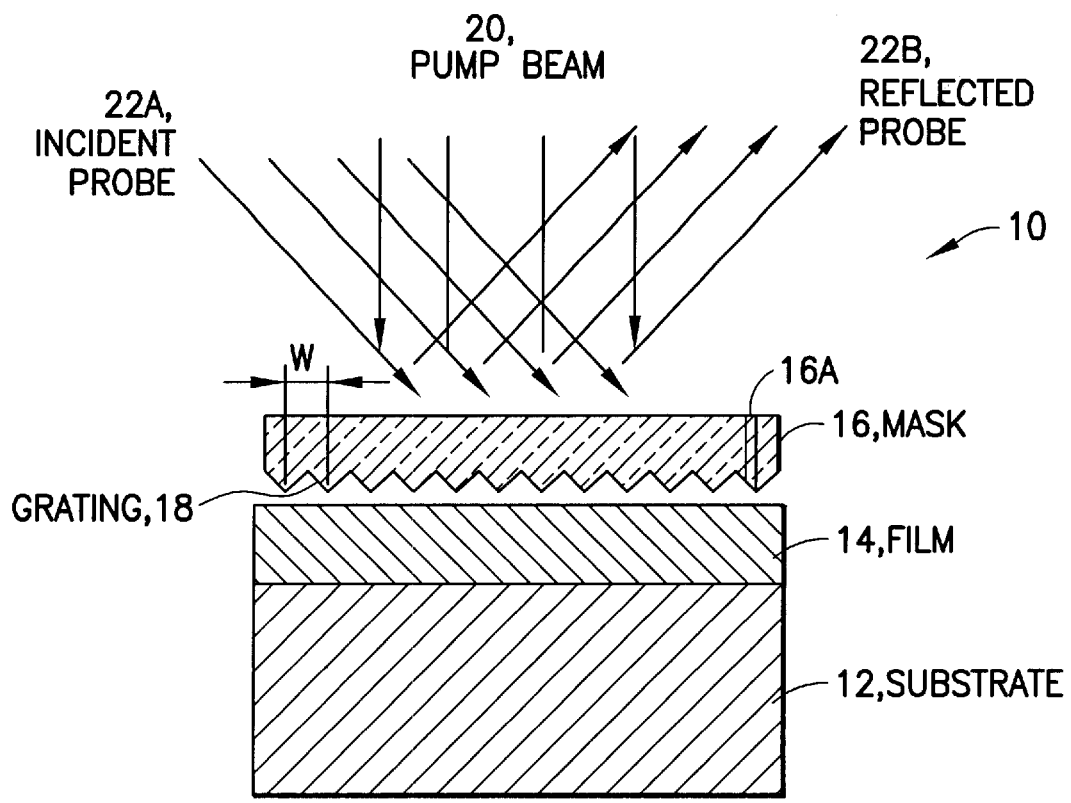
FIG. 1 is an enlarged, cross-sectional view, not to scale, of a sample having a substrate, at least one film, and a mask disposed over a surface thereof in accordance with these teachings.

Referring first to FIG. 1, a sample 10 includes a substrate 12, such as semiconductor material (e.g., silicon, a Group III–V material, or a Group II–VI material) having at least one film 14, such as a metal film or semiconductor or a dielectric film, disposed on or over a top surface thereof. A transparent plate, referred to herein as a mask 16, is placed on top of the sample 10. The mask 16 has a periodic grating 18 formed on or within a lower surface thereof. A pump light pulse 20 from a pump light source 30 (FIG. 2) is directed through the mask 16 onto the sample 10, specifically onto the free (upper) surface of the film 14. The mask 16 distorts the wavefront of the pump light pulse and, as a result, the intensity of the light incident onto the free surface of the film 14 varies periodically with position across the sample's surface. This causes a heating of the surface of the film 14 that varies in a spatially periodic manner as a function of position. The regions of the film 14 that are heated expand. As a result, strain pulses are launched into the sample 10 from each of the expanding regions. These strain disturbances result in a change in the optical constants of the sample 10, and this change is detected by means of a time-delayed probe pulse 22A that is also directed onto the sample 10 through the mask 16, specifically by detecting (in this embodiment) a reflected portion 22B of the probe pulse. The probe pulse 22A originates from a probe source 32, which could be the pump source 30 as well. Preferably, the pump and probe pulses are laser pulses of picosecond or sub-picosecond duration, and originate from one laser or from two lasers. As in the standard method and the grating method, one or more characteristics of the sample 10 may be determined, such as those listed above.

Figure 2:
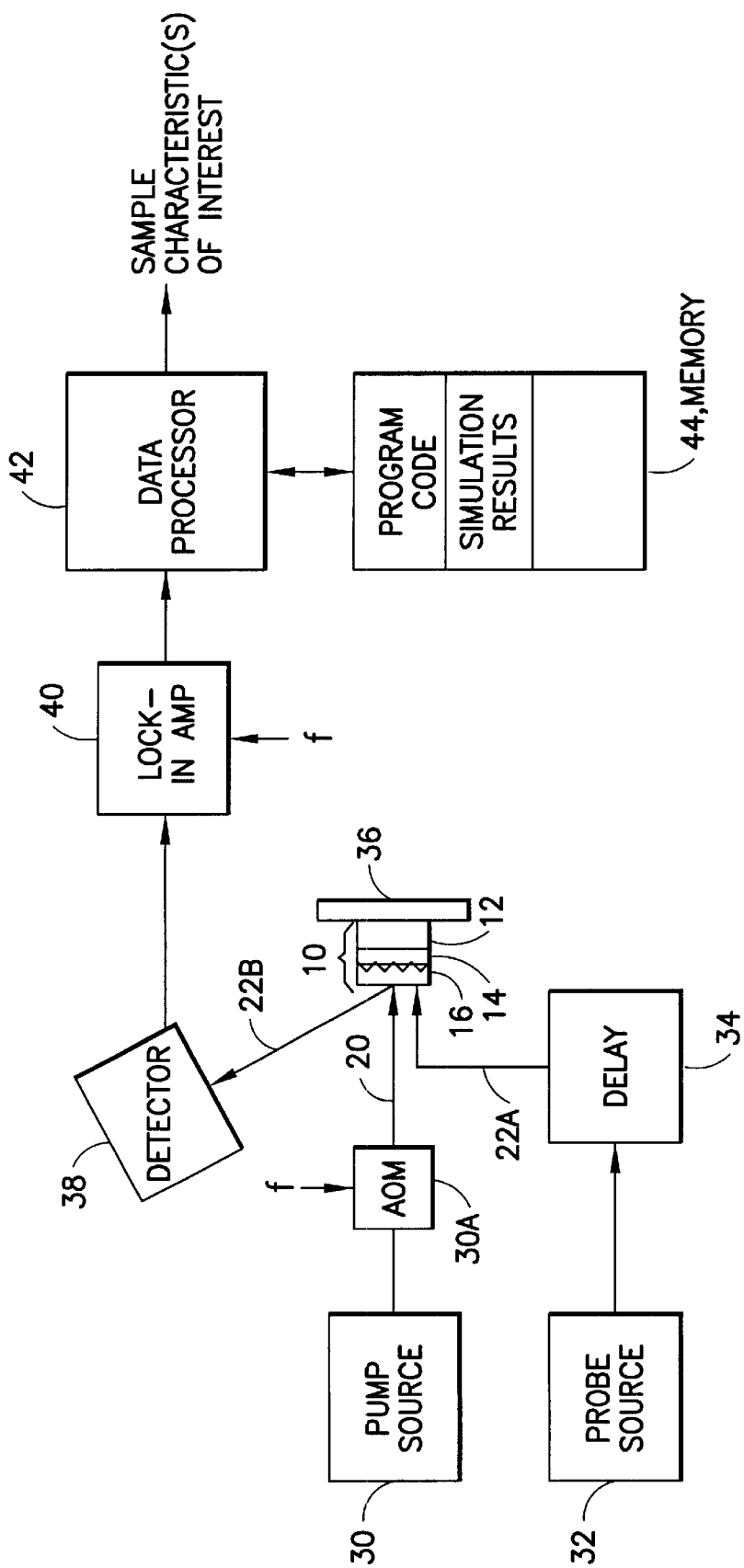
FIG. 2 is a simplified block diagram of a material characterization system in accordance with these teachings.

In one preferred embodiment, and referring as well to FIG. 2, the pump and probe beams 20, 22A are directed through the mask 16 at normal incidence. The probe beam 22A is delayed relative to the pump beam 20, preferably by means of a variable optical path 34 provided by a movable stage or by some other technique. The sample 10 is assumed to be supported by some suitable type of fixed or movable sample stage 36. The change in the intensity of the reflected probe beam 22B is sensed by a detector 38 and measured as a function of a time delay t between the application of the pump and probe pulses 20, 22A. To improve the signal to noise ratio the intensity of the pulses composing the pump beam 20 can be modulated at some frequency f by means of an acousto-optic modulator (AOM) 30A. The output of the detector 38, which is an electrical signal indicative of the intensity of the reflected probe beam 22B, is fed into a lock-in amplifier 40 for which the reference signal is at the same frequency f as the modulation frequency of the AOM 30A. A data processor 42 has an input coupled to an output of the lock-in amplifier 40, and is further coupled to a memory 44, such as a hard disk, RAM, ROM, etc., wherein is stored an operating program, simulation results and other required data, constants and the like. The measured change $\Delta R(t)$ in reflectivity is compared by the data processor 42 with the results of a simulated reflectivity change $\Delta R_{sim}(t)$ stored in the memory 44.

Figure 3:
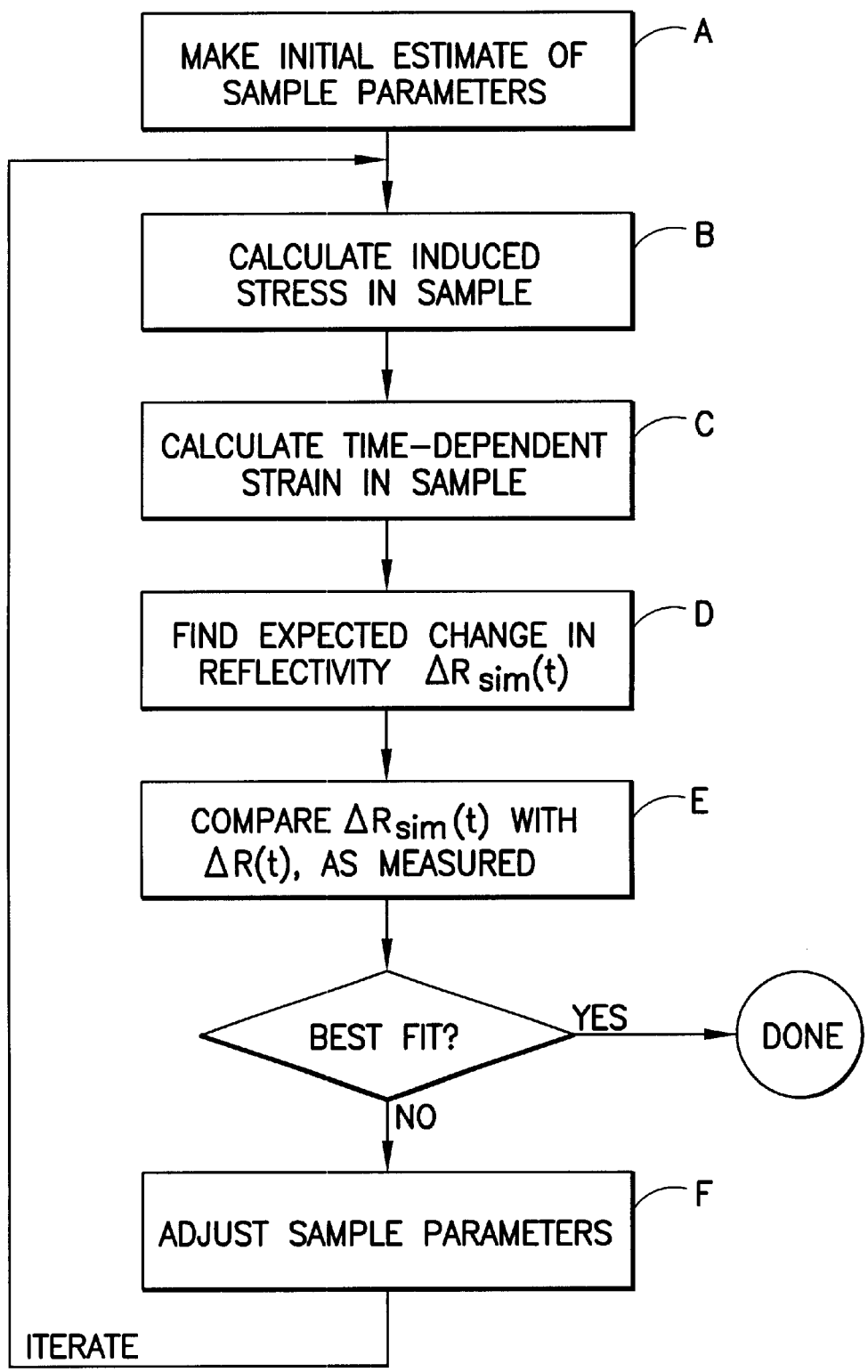
FIG. 3 is a logic flow diagram of a method for operating the data processor shown in FIG. 2 for generating a simulation of a change in sample reflectivity, and for comparing the simulation to a measured change in sample reflectivity.

The change $\Delta R_{sim}(t)$ is preferably determined in accordance with the following method. Reference can also be made to the logic flow diagram of FIG. 3.

At Step A an initial estimate is made for the parameters of the sample 10. These parameters include, but are not necessarily limited to, the thickness, density, sound velocity, thermal expansion, specific heat, optical constants of the different films, the adhesion between the films, the orientation of crystalline grains making up a film, the size of grains, the crystal phase and electrical resistivity of each film.

Based on the assumed values, at Step B the stress in the sample 10 that is induced by the pump light pulse 20 is calculated.

At Step C, the time-dependent strain in the sample 10 is calculated.

From the calculated strain, at Step D the expected change in reflectivity $\Delta R_{sim}(t)$ is found.

At Step E, the expected change in reflectivity $\Delta R_{sim}(t)$ is compared with the measured change in reflectivity $\Delta R(t)$.

At Step F, the parameters of the sample are adjusted and the procedure iterated one or more times in order to achieve the best possible agreement between $\Delta R(t)$ and $\Delta R_{sim}(t)$.

For certain samples, it may be possible to simplify the procedure just described. Consider first a sample 10 that includes a single film 14 deposited onto the substrate 12 (as in FIG. 1), where the thickness d of the film 14 is significantly greater than the spacing w of the grating lines 18 on the mask 16. For a time t less than the time required for a strain pulse to propagate through the thickness of the film 14 to the substrate 12 and return to the top surface of the film 14, the reflectivity change $\Delta R(t)$ is unaffected by the existence of the substrate 12, i.e., the response $\Delta R(t)$ is the same as would be obtained on a bulk material of the same composition and material properties as the film 14. The stress set up by the pump pulse 20 excites a Rayleigh surface wave that is confined to the region near to the upper surface of the film 14. This wave may be considered to be a standing wave of wavelength $\lambda = w$. The frequency of this standing wave is given by $f_R = c_R/w$ where $c_R$ is the Rayleigh wave velocity. The presence of this standing wave causes a periodic modulation of the elastic strain in the surface layer of the film 14, which in turn causes a contribution to $\Delta R(t)$ that varies in time with the frequency $f_R$. An analysis of the measured $\Delta R(t)$ can be used to obtain the frequency $f_R$, and from this frequency, and from the known value of w, the Raleigh wave velocity of the material of the film 14 can be found. This velocity can be expressed in terms of the elastic constants of the film material using a well-known formula.

One reference for the velocity of a Rayleigh surface wave is L. D. Landau and E. M. Lifshitz, "Theory of Elasticity", second edition, Pergamon Press, 1970, section 24. The theory of Rayleigh velocity in elastically anisotropic crystals is complicated but, in general, for an elastically isotropic solid, $c_R$ is given as follows. First define the quantity $\zeta = c_R/c_T$. It can then be shown (see Landau et al.) that $\zeta$ is the solution for the following equation:

$$\xi^6 - 8\xi^4 + 8\xi^2\left(3 - 2\frac{c_T^2}{c_L^2}\right) - 16\left(1 - \frac{c_T^2}{c_L^2}\right) = 0$$

where $c_t$ and $c_L$ are the velocities of longitudinal and transverse sound, respectively.

If the material of the film 14 is elastically isotropic, a knowledge of the Rayleigh velocity, together with an assumed value for Poisson's ratio, can be used to estimate the longitudinal and transverse sound velocities in the material of the film 14.

More specifically, the ratio of the velocity of the transverse and longitudinal sound is given by $$\frac{C_T}{C_L} = \sqrt{\frac{1-2\sigma}{2(1-\sigma)}}.$$

Therefore, $$\xi^6 - 8\xi^4 + 8\xi^2 \frac{2-\sigma}{1-\sigma} - 16\frac{1}{2(1-\sigma)} = 0$$

Hence, if σ is known, the value of ξ can be calculated from the preceding equation. A measurement of $c_R$ can then be used to give $c_t$ via the relation $$C_T = \frac{C_R}{\xi},$$

and $c_L$ can be found from $$C_L = C_T\sqrt{\frac{2(1-\sigma)}{1-2\sigma}} = \frac{C_R}{\xi}\sqrt{\frac{2(1-\sigma)}{1-2\sigma}}.$$

For this type of sample, a strain pulse will also propagate away from the surface of the film 14 and into the volume of the film 14. The strain pulse is partially reflected at the interface between the film 14 and the substrate 12, and returns to the free (upper) surface of the film 14. The return of the reflected strain pulse results in a sharp feature in ΔR(t) at a time $\tau_L$ equal to $2w/c_L$, where $c_L$ is the longitudinal sound velocity. Hence, this time can be used to determine the thickness of the film 14. The value of $c_L$ can be estimated from the results of the measurements of the Rayleigh velocity as described above. Alternatively, for films of known composition and elastic properties, the value of $c_L$ can be taken from the scientific literature.

A simplified analysis can also be made for those samples 10 in which the thickness of the film 14 is much less than the grating period w. In this case the penetration depth of the Rayleigh wave is greater than the thickness of the film 14. Thus, the Rayleigh wave will not be confined within the film thickness and will penetrate into the substrate 12. The velocity of the Rayleigh wave is now dependent on the elastic properties and densities of both the film 14 and the substrate 12, and is also affected by the thickness of the film 14. Measurement of the frequency of the oscillations in ΔR(t) gives the Rayleigh wave velocity. There is also a component of the strain that propagates through the thickness of the film 14 and that is reflected back at the interface with the substrate 12, thereby giving the sharp feature in ΔR(t) at a time $2w/c_L$. Again, from the measured Rayleigh wave velocity $c_R$ and the time $\tau_L$, the longitudinal and transverse sound velocity, and the thickness of the film 14, can be determined.

It is within the scope of these teachings to make a number of variations in these measurement techniques.

For example, the pump light pulse 20 and the measuring probe light pulse 22A can be directed at the surface of the sample 10 at normal or oblique incidence. Furthermore, the angle of incidence of the probe pulse 22A can be the same as the angle of incidence of the pump pulse 20, or the angle of incidence of the probe pulse 22A may be different than the angle of incidence of the pump pulse 20. Also, the wavelength of the pump and probe beams 20, 22A can be the same, or they can be different. If the wavelengths are different, and for the case where it is desired to detect a diffracted probe beam, the wavelength of the probe beam 22A is set to be less than the line spacing of the mask 16.

In the description given above, the detection of the time varying strain in the sample 10 is made through a measurement of the change in the intensity of the reflected probe light 22B. However, it is also within the scope of these teachings for measurements to be made of the change in the intensity of transmitted (as opposed to reflected) probe light. Also, measurements can be made of a change in the polarization of the reflected or transmitted probe light, a change in the optical phase of the reflected or transmitted probe light, or a change in propagation direction of the reflected or transmitted probe light. Measurements may be made of more than one of these characteristics, such as a measurement of intensity of the reflected or transmitted probe light and a measurement of optical phase of the reflected or transmitted probe light.

Further by example, a measurement could be made of the intensity of the transmitted probe light in conjunction with a measurement of optical phase of the reflected probe light.

The pump and/or the probe light can be brought to the mask 16 through free space or through optical fiber(s). Measurements can be made of the component of the probe light that is specularly reflected from the sample (angle of reflection equal to angle of incidence), or diffracted at an angle as a result of the presence of the grating in the mask 16, or from that part of the probe light that is scattered diffusely from the surface of the sample 10.

The mask 16 can be made of a number of transparent materials, such as silica, other glasses, or polymers. It is straightforward to obtain gratings that have a line spacing as small as 2000 Å, and this distance can be made even smaller through the use of electron beam lithography.

The mask 16 can also be constructed using a slab of a transparent material with opposing flat surfaces, and the grating 18 formed with a patterned thin film of a dielectric material, or with a metal deposited onto its lower surface. The thickness of the mask 16 need not be uniform, as a wedged or tapered thickness mask could be used as well.

Furthermore, a single mask 16 could have two or more gratings 18 on the lower surface, where each grating has different line spacings. In this case the pump and probe beams 20, 22A could be directed to different regions of the mask 16 where the spacing of the grating 18 has a chosen value, and in this way a measurement of ΔR(t) can be made for two or more different values of the spacing w of the lines on the grating 18. Alternatively, the pump and probe beams 20, 22A can be directed to a fixed location on the surface of the sample 10, and the mask 16 moved, using a mask positioning system 46 (FIG. 4), so that regions of the mask 16 with different grating line spacing are positioned in the region where the pump and probe beams are located.

In some applications it may advantageous to use a mask 16 having a two dimensional array of grating features (e.g., a square array), rather than a sequence of lines (one-dimensional array).

Figure 4:
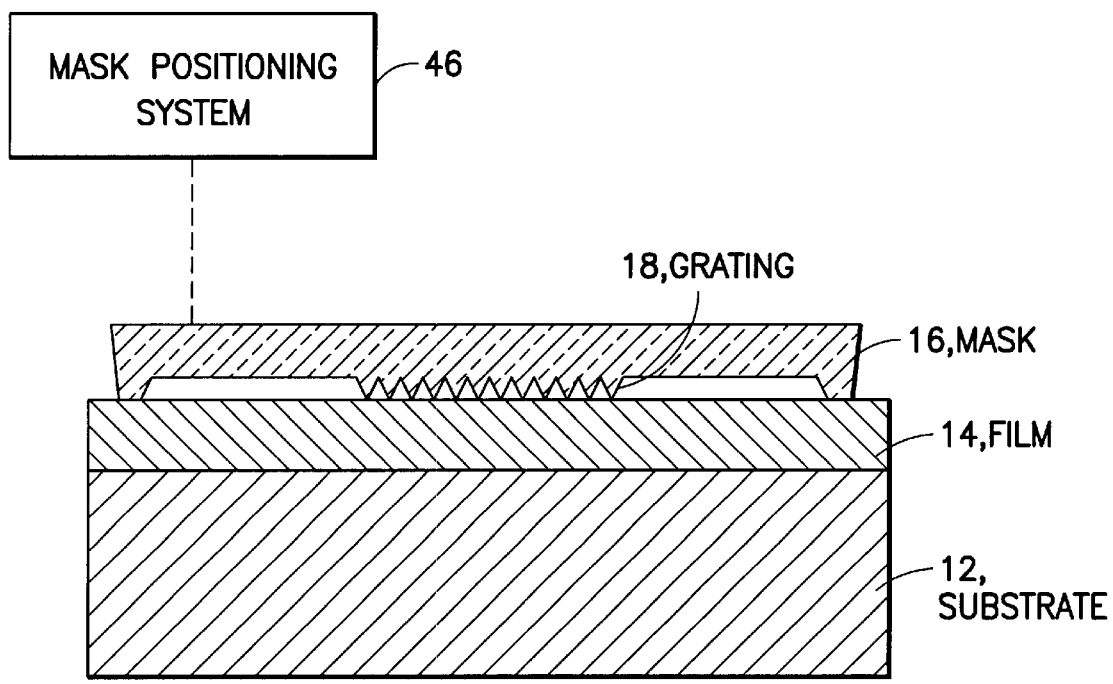
FIG. 4 is an enlarged, cross-sectional view, not to scale, of a sample having a substrate, at least one film, and a mask disposed over a surface thereof in accordance with a further embodiment of these teachings, wherein the grating region of the mask is at a different height than all or a portion of the surrounding area of the lower surface of the mask.

The mask 16 can be positioned by the mask positioning system 46 by being placed in direct contact with the sample surface, i.e., with the free (upper) surface of the film 14. It is also possible through the use of nanomachining techniques to construct a mask 16 that is prevented from coming into direct contact with the free surface of the film 14 by means of an air cushion produced by passing air through small holes 16A in the mask 16, as is done, for example, in an air track used in physics teaching laboratories. In this case the spacing of the mask 16 from the surface of the film 14 is preferably no larger than the spacing between the lines of the grating 18. It is also within the scope of these teachings to construct a mask 16 that has the grating 18 in a center section that is lower than most or all of a surrounding area of the mask 16, as shown in FIG. 4. That is, the grating portion of the lower surface of the mask 16 is not coplanar with the surrounding surface area. This approach is useful for those samples 10 that have surfaces that are not flat, as it ensures that the grating 18 can be placed in close proximity to the surface of the film 14.

The mask 16 can be lowered onto the sample 10 and raised from the surface of the sample 10 by the mask positioning system 46 using a number of different techniques. For example, electrical or magnetic forces can be applied to the mask 16, or the mask 16 can be raised or lowered by means of air currents.

Figure 6:
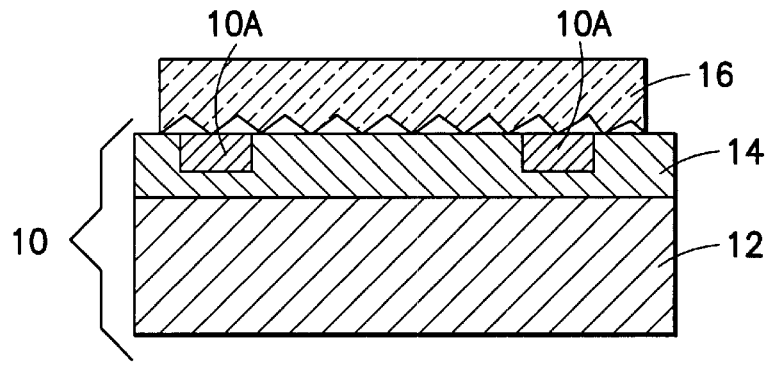
FIG. 6 depicts in an enlarged cross-section a sample having laterally patterned features.

Measurements can be made on a single film 14 on a substrate 12, on a stack of thin films of different thickness and material composition, or on samples 10 that are laterally patterned. For example, FIG. 6 shows a sample 10 having laterally patterned features 10A, such as embedded metalization lines, and the mask 16 positioned over a surface of the sample 10 in accordance with the teachings herein. The metalization lines need not be embedded, and could as well be located on a top surface of the film 14. In this embodiment it may be advantageous to make the period of the mask 16 match the period of the features 10A, or to mismatch the period of the mask 16 with the period of the features 10A. It may also be advantageous to provide a predetermined relationship between the size(s) of features 10A and the period(s) of the mask 16 (where the mask 16 can be provided with two or more characteristic periods for the grating 18, or where more than one mask is used).

Based on the foregoing it can be appreciated that these teachings overcome the problems discussed above with relation to the prior art. For example, the sound velocity in the sample can be measured directly, and need not be known a priori. Furthermore, the use of the mask relaxes the requirement that the sample characterization apparatus be constructed so as ensure that the phase relation between a plurality of pump beams remains constant, as a single pump beam is sufficient to provide the spatially distributed heating effect at the surface of the sample.

In addition to the changes in reflectivity arising from the strain pulses that are launched in the sample 10, there can be changes in reflectivity that arise from the change in the temperature, and in the density of electrons and holes. The change in reflectivity arising from these effects can be distinguished from the change in reflectivity that arises from the propagation of strain pulses.

More particularly, strain pulses give rise to either sharp pulses (from sound echoing back and forth in a film) or to an oscillatory contribution (from the Rayleigh surface waves), while the contribution to the change in reflectivity that arises from the change in temperature or from the change in the electron and hole concentration varies more smoothly with time.

The teachings of this invention also make it possible to measure the electrical resistivity of a metal film, provided that the film has a thickness lying within a certain range. In this embodiment, a determination is first made of the thermal conductivity $\kappa_{film}$ of the metal film. From $\kappa_{film}$ the electrical resistivity $\rho_{film}$ can be calculated using the Wiedemann-Franz law:

$$\rho_{film} = \frac{LT}{\kappa_{film}},$$

where L is the Lorenz number and T is the absolute temperature (see, for example, C. Kittel, Introduction to Solid State Physics, 7$^{th}$ edition, Wiley, p. 168).

The following is a method for the determination of the thermal conductivity. Consider a metal film of thickness d deposited onto a substrate. Let the mask have a line spacing w with lines running parallel to the y axis, and let the normal to the substrate be in the z direction. Assume that the intensity $I_{pump}(x)$ of the pump light varies with position on the sample surface according to $$I_{pump}(x) = I^o_{pump}[1 + \cos(kx)],$$

where $I^o_{pump}$ is a constant, $\kappa = 2\pi n/w$, and x is an axis running across the surface in a direction perpendicular to the direction of the lines. The form of the intensity variation across the surface of the sample is dependent on the geometry of the mask 16 and on its optical properties. The particular form given above is for illustration and is not intended to imply that this variation will occur for all masks 16. The pump light pulse induces a temperature rise $\Delta T$ that varies across the sample surface. Again, for illustration, we take this to have the same form:

$$\Delta T(x, z=0) = \Delta T_0[1 + \cos(kx)],$$

where $\Delta T_0$ is a constant. This is the temperature at the surface located on the plane z=0; the temperature rise at a distance below the surface will be less. The variation of the temperature rise with distance z into the film is determined by: 1) the distance $\zeta$ that the light penetrates into the metal, 2) by the distance $\xi$ that the conduction electrons that are excited by the light diffuse before they lose their energy to the thermal phonons and come into thermal equilibrium with the lattice (see G. Tas and H. J. Maris, Electron Diffusion in Metals Studied by Picosecond Ultrasonics, Physical Review B 49, 15046 (1994)), and 3) by the film thickness. Note that since the lines on the mask 16 run parallel to the y-axis there is no dependence of the temperature on the coordinate y.

The change in temperature of the sample surface results in a change in the optical reflectivity that is different at each point on the surface. In the absence of the mask 16 it is reasonable, as a first approximation, to consider that the change in reflectivity of the probe beam due to the temperature change would be proportional to the average of the change in temperature taken over the area of the surface onto which the probe light is incident. However, it is important to recognize that the mask 16 distorts the probe beam so that, just like the pump beam, it has a greater intensity at some points on the surface of the sample 10 than at others. If one take the intensity of the probe light at the surface of the sample 10 to vary with position as:

$$I_{probe}(x) = I^o_{probe}[1 + \cos(kx)],$$

where $I^o_{probe}$ is a constant, then the change $\Delta R$ in reflectivity is proportional to the average over the surface of the product of the probe intensity with the temperature change at the surface, i.e., $$\Delta R \int dx I_{probe}(x) \Delta T(x, z=0)$$

$$I_{probe}[A+B],$$

where $$A \equiv \int dx \Delta T(x, z=0)$$

$$B \equiv \int dx \cos(kx) \Delta T(x, z=1)$$

At a time t after the application of the pump pulse, the temperature distribution in the film will have changed because of heat flow. A measurement of $\Delta R(t)$ as a function of time can provide information about this heat flow. It should be noted that the reflectivity change $\Delta R$ contains the term A which is proportional to the temperature change of the film averaged across its surface, and also contains the term B that vanishes when the temperature distribution across the film surface is uniform. Thus, $\Delta R(t)$ is affected both by heat flow out of the film into the substrate (this primarily affects the term A), as well as by heat flow within the film which tends to make the temperature distribution across the surface of the film uniform, and hence reduces the magnitude of the term B.

The heat flow within the metal film may have components both parallel and perpendicular to the plane of the film. The heat flux $\bar{q}$ at any point is equal to $\kappa_{film}\Delta T$, where $\kappa$film is the thermal conductivity of the metal film. The heat flow across the interface into the substrate per unit area is equal to $\sigma_K \Delta T_{int}$, where $\Delta T_{int}$ is the temperature jump across the interface and $\sigma_K$ is the Kapitza conductance at the interface. Note that since $\Delta T_{int}$ is the difference between the temperature of the film and the temperature of the substrate, this heat flow is also affected by the thermal conductivity $\kappa_{sub}$ of the substrate.

Figure 5:
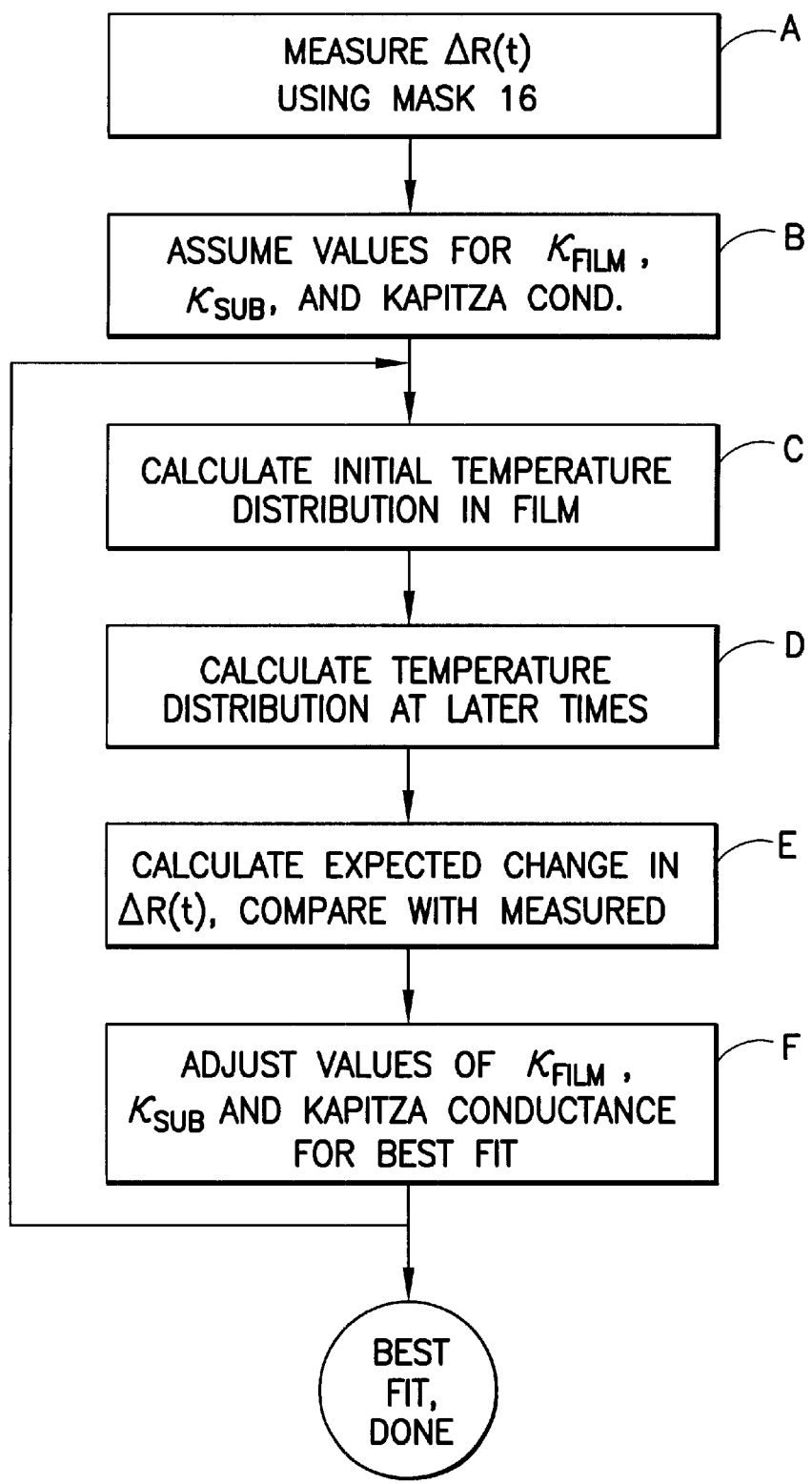
FIG. 5 is a logic flow diagram of a method for the determination of the electrical resistivity of a metal film using the optical mask in accordance with the teachings herein.

Referring now to FIG. 5, one procedure for the determination of the electrical resistivity of the metal film is as follows:

Step (A): $\Delta R(t)$ is measured as a function of the time t after the application of the pump pulse using a mask of known repeat distance w.

Step (B): Values are assumed for the thermal conductivity $\kappa_{film}$ of the film, the thermal conductivity $\kappa_{sub}$ of the substrate, and the Kapitza conductance $\sigma_K$ between the film and the substrate.

Step (C): The initial temperature distribution within the film is calculated. This calculation is preferably based on the known geometry, line spacing or repeat distance w and on the optical characteristics of the mask 16. The temperature distribution is affected by the diffusion coefficient of the hot electrons excited by the pump pulse. This diffusion coefficient can be estimated from the assumed value of the thermal conductivity of the film, as described by Tas and Maris in the publication referenced above.

Step (D): The temperature distribution within the film is then calculated at later times based on the assumed values for the thermal conductivity of the film, the thermal conductivity of the substrate, and the Kapitza conductance between the film and the substrate.

Step (E): The expected change in reflectivity $\Delta R(t)$ based on the temperature distribution determined in Step (D) is then calculated.

Step (F) The parameters $\kappa_{film}$, $\kappa_{sub}$, and $\sigma_K$, are then adjusted, and Steps (C)–(E) are repeated so as to obtain a best fit to the measured $\Delta R(t)$.

The electrical resistivity of the film is then calculated using the thermal conductivity, as described above.

It is important to note that the optimum choice of the repeat distance w of the mask 16 depends on the thickness d of the film and on the values of $\kappa_{film}$, $\kappa_{sub}$, and $\sigma_K$. For example, if w is chosen to be too small, the hot electrons will diffuse so far that the initial temperature distribution will be almost uniform across the surface of the film, i.e., the temperature distribution in the film will be independent of x. The term B will then be absent. Suppose now that it is also true that the thickness of the film d is less than the diffusion length $\xi$. In this case the initial temperature distribution throughout the film will be uniform. As a result, the temperature at later times, and hence also the reflectivity change $\Delta R(t)$, will only be affected by the Kapitza conductance $\sigma_K$. Under these conditions, the measurement of $\Delta R(t)$ generally cannot be readily analyzed to determine the thermal conductivity of the film.

It is noted that if the mask 16 is not used, the initial temperature distribution would be uniform across the sample surface. For films whose parameters d, $\kappa_{film}$, $\kappa_{sub}$, and $\sigma_K$ lie in a suitable range it would be possible to perform an analysis of the measured $\Delta R(t)$ to determine $\kappa_{film}$. However, the range of film parameters for which the accurate determination of $\kappa_{film}$ is possible is greatly increased through the use of a mask 16 of suitably chosen repeat distance w.

It is within the scope of the teachings of this invention to make measurements on a single sample using a series of masks 16 of different repeat distances w, and to fit the totality of results so obtained by adjustment of the parameters $\kappa_{film}$, $\kappa_{sub}$, and $\sigma_K$.

As an alternate method, one may compare the measured $\Delta R(t)$ on a sample of unknown resistance with the results of measurements of $\Delta R(t)$.

The mask 16 can also be used to advantage for the characterization of samples 10 into which ions have been implanted (or, more generally, the mask 16 may be used with altered materials). Reference with regard to such altered materials may be made to U.S. Pat. No. : 5,706,094, "Ultrafast Technique for the Characterization of Altered Materials", by H. J. Maris, as well as to U.S. Pat. No. : 6,008,906, "Optical Method for the Characterization of the Electrical Properties of Semiconductors and Insulating Films"[1], by H. J. Maris.

In general, the characteristics of a sample 10 that has been ion implanted are affected by the following parameters:

(A) the number of ions implanted per unit area of the surface of the sample 10, referred to as the dose;

(B) the kinetic energy of the ions that are directed at the sample surface, referred to as the energy;

(C) the direction at which the ion beam is incident onto the sample 10;

(D) the ion current per unit area during the implant process;

(E) the species of the implanted ion;

(F) the charge on the ion, e.g., singly or double ionized;

(G) the duration of time that the ion-implanted sample 10 is annealed; and (H) the temperature at which the ion-implanted sample 10 is annealed.

In the above-referenced U.S. Pat. No. : 5,706,094 it was disclosed to investigate as many as possible of these characteristics through measurements of the change in reflectivity $\Delta R(t)$ of the probe pulse applied directly to the surface at a time t after the application of the pump pulse. Experimental parameters that were varied included the wavelength of the pump and/or the probe light, where a change in wavelength changes the distance over which the pump and probe light is absorbed; and the intensity of the pump and/or the probe light, which changes the density of electrons and holes excited in the sample.

While a variation in the wavelength and/or the intensity can be helpful in providing a more extended characterization of a sample, it may be difficult to obtain a complete characterization of a sample 10 by these means alone, given the large number of sample parameters that can affect the measurement. In addition, while it is possible to build an instrument in which the wavelength of the pump and/or the probe light can be selected to have two different values (for example, by the use of a frequency doubling crystal), it can be difficult to build an instrument in which the pump and probe wavelengths are continuously adjustable.

The use of present invention has the advantage that the repeat distance w of the mask 16 can be selected so as to optimize the amount of information that can be obtained for a particular type of sample. The mask repeat distance can also be selected so as to make the measured $\Delta R(t)$ particularly sensitive to one or more of the sample characteristics (A)–(H) listed above. Furthermore, measurements can be made for a number of different mask 16 repeat distances w in order to achieve a more complete characterization. Also, measurements can be made for line masks or for masks 16 with two dimensional arrays of features.

For the analysis of the data, the most practical method in many applications may be by comparison with data taken on reference samples of known characteristics. However, the data analysis may also be performed by comparison of the data to simulations, together with adjustment of parameters and iteration to achieve a best fit.

While the invention has been particularly shown and described with respect to preferred embodiments thereof, it will be understood by those skilled in the art that changes in form and details may be made therein without departing from the scope and spirit of the invention.

What is claimed is:

1. A method for determining at least one characteristic of a sample comprising a substrate and at least one film disposed on or over a surface of the substrate, comprising steps of:

placing a mask over a free surface of the at least one film, the mask having a top surface and a bottom surface that is placed adjacent to the free surface of the film, the bottom surface of the mask comprising a plurality of features forming at least one grating;

directing optical pump pulses through the mask to the free surface of the film, individual ones of the pump pulses being followed by at least one optical probe pulse, said pump pulses being spatially distributed by said at least one grating for launching a plurality of spatially distributed strain pulses within the film, said strain pulses causing a change in optical constants of the film;

detecting a reflected or transmitted portion of said probe pulses, said probe pulses also being spatially distributed by said at least one grating;

measuring a change in at least one characteristic of at least one of reflected or transmitted probe pulses due to the change in optical constants; and determining the at least one characteristic of the sample from the measured change in the at least one characteristic of the probe pulses.

2. A method as in claim 1, wherein the determined at least one characteristic of the sample is film thickness.

3. A method as in claim 1, wherein the determined at least one characteristic of the sample is an adhesion between the film and the substrate.

4. A method as in claim 1, wherein the determined at least one characteristic of the sample is an adhesion between the film and another film.

5. A method as in claim 1, wherein the determined at least one characteristic of the sample is an orientation of crystalline grains that comprise the film.

6. A method as in claim 1, wherein the determined at least one characteristic of the sample is a size of crystalline grains that comprise the film.

7. A method as in claim 1, wherein the determined at least one characteristic of the sample is a crystal phase of a film.

8. A method as in claim 1, wherein said pump pulses being spatially distributed by said at least one grating induce a spatial variation in temperature of the film, wherein the variation in temperature causes a change in optical constants of the film, and where the determined at least one characteristic of the sample is an electrical resistivity of the film.

9. A method as in claim 1, wherein the determined at least one characteristic of the sample is a rate of electromigration within the film.

10. A method as in claim 1, wherein the determined at least one characteristic of the sample is a yield stress of the film.

11. A method as in claim 1, wherein the step of determining the at least one characteristic of the sample comprises steps of:

simulating a response of the sample to the application of the pump pulses through said mask using assumed sample properties;

comparing the measured change in the least one characteristic of the probe pulses to the simulated response; and changing the assumed sample properties, and repeating the steps of simulating and comparing until the measured change agrees with a result of the simulation.

12. A method as in claim 1, wherein the step of measuring measures at least one of an intensity of reflected or transmitted probe pulses; a polarization of reflected or transmitted probe pulses, a change in an optical phase of reflected or transmitted probe pulses, and a change in a propagation direction of reflected or transmitted probe pulses.

13. A method as in claim 1, wherein said mask has a period that is a function of a thickness of said at least one film.

14. A method as in claim 1, wherein said mask has a period that is greater than a thickness of said at least one film.

15. A method as in claim 1, wherein said mask has a period that is less than a thickness of said at least one film.

16. A method as in claim 1, wherein said pump pulses excite a Rayleigh standing surface wave in the film of wavelength $\lambda = w$, where w is the grating period, the Rayleigh standing surface wave having a frequency given by $f_R = C_R/w$, where $c_R$ is the Rayleigh wave velocity, the standing wave causing a periodic modulation of elastic strain in the film which in turn causes a contribution to $\Delta R(t)$ th at varies in time with the frequency $f_R$, further comprising steps of:

analyzing a measured $\Delta R(t)$ to obtain the frequency $f_R$, and from this frequency, and from a known value of w, determining the Raleigh wave velocity of material that comprises the film; and using the determined Rayleigh wave velocity, together with a value for Poisson's ratio, estimating longitudinal and transverse sound velocities in the material that comprises the film.

17. A method as in claim 16, wherein for a case where w is less than a thickness of the film, strain pulses are partially reflected at an interface between the film and the substrate and return to the upper surface of the film resulting in a sharp feature in $\Delta R(t)$ at a time $\tau_L$ equal to $2w/c_L$, where $c_L$ is the longitudinal sound velocity, and further comprising a step of determining the thickness of the film using the time $\tau_L$.

18. A method as in claim 16, wherein for a case where w is greater than a thickness of the film, wherein the velocity of the Rayleigh wave is dependent on elastic properties and densities of both the film and the substrate, and is also dependent on the thickness of the film, further comprising steps of:

measuring frequency of oscillations in $\Delta R(t)$ to obtain the Rayleigh wave velocity $c_R$;

detecting a component of the strain pulse that propagates through the thickness of the film and that is reflected back at the interface with the substrate, thereby giving a sharp feature in $\Delta R(t)$ at a time $2w/c_L$; and using the determined Rayleigh wave velocity $c_R$ and a time $\tau_L$ equal to $2w/c_L$, where $c_L$ is the longitudinal sound velocity, determining the longitudinal and transverse sound velocity and the thickness of the film.

19. A method as in claim 1, wherein at least one of the pump pulses and the probe pulses are directed through the mask at normal incidence to the free surface of the film.

20. A method as in claim 1, wherein at least one of the pump pulses and the probe pulses are directed through the mask at oblique incidence to the free surface of the film.

21. A method as in claim 1, wherein the sample comprises features that are laterally patterned.

22. A system for determining at least one characteristic of a sample comprising a substrate and at least one film disposed on or over a surface of the substrate, comprising:

a mask adapted for being placed over a free surface of the at least one film, the mask having a top surface and a bottom surface that is placed adjacent to the free surface of the film, the bottom surface of the mask comprising a plurality of features forming at least one grating;

an optical system for directing optical pump pulses through the mask to the free surface of the film, individual ones of the pump pulses being followed by at least one optical probe pulse, said pump pulses being spatially distributed by said at least one grating for launching a plurality of spatially distributed strain pulses within the film, said strain pulses causing a change in optical constants of the film;

an optical detector for detecting a reflected or transmitted portion of said probe pulses, said probe pulses also being spatially distributed by said at least one grating; and a data processor for measuring a change in at least one characteristic of at least one of reflected or transmitted probe pulses due to the change in optical constants and for determining the at least one characteristic of the sample from the measured change in the at least one characteristic of the probe pulses.

23. A system as in claim 22, wherein the determined at least one characteristic of the sample is selected from one of film thickness, an adhesion between the film and the substrate, an adhesion between the film and another film, an orientation of crystalline grains that comprise the film, a size of crystalline grains that comprise the film, a crystal phase of a film, a rate of electromigration within the film, and a yield stress of the film, further wherein said pump pulses being spatially distributed by said at least one grating induce a spatial variation in temperature of the film, wherein the variation in temperature causes a change in optical constants of the film, and where the determined at least one characteristic of the sample is an electrical resistivity of the film.

24. A system as in claim 22, wherein said data processor operates to simulate a response of the sample to the application of the pump pulses through said mask using assumed sample properties, to compare the measured change in the least one characteristic of the probe pulses to the simulated response, and to change the assumed sample properties and iteratively simulate and compare until the measured change agrees with a result of the simulation.

25. A system as in claim 22, wherein said data processor measures at least one of an intensity of reflected or transmitted probe pulses; a polarization of reflected or transmitted probe pulses, a change in an optical phase of reflected or transmitted probe pulses, and a change in a propagation direction of reflected or transmitted probe pulses.

26. A system as in claim 22, wherein said mask has a period that is a function of a thickness of said at least one film.

27. A system as in claim 22, wherein said pump pulses excite a Rayleigh standing surface wave in the film of wavelength $\lambda=w$, where w is the grating period, the Rayleigh standing surface wave having a frequency given by $f_R=c_R/w$, where $c_R$ is the Rayleigh wave velocity, the standing wave causing a periodic modulation of elastic strain in the film which in turn causes a contribution to $\Delta R(t)$ that varies in time with the frequency $f_R$, and where said data processor operates to analyze a measured $\Delta R(t)$ to obtain the frequency $f_R$, and from this frequency, and from a known value of w, to determine the Raleigh wave velocity of material that comprises the film; and further operates, using the determined Rayleigh wave velocity, together with a value for Poisson's ratio, to estimate longitudinal and transverse sound velocities in the material that comprises the film.

28. A system as in claim 27, where for a case where w is less than a thickness of the film, strain pulses are partially reflected at an interface between the film and the substrate and return to the upper surface of the film resulting in a sharp feature in $\Delta R(t)$ at a time $\tau_L$ equal to $2w/c_L$, where $c_L$ is the longitudinal sound velocity, and where said data processor determines the thickness of the film using the time $\tau_L$.

29. A system as in claim 27, where for a case where w is greater than a thickness of the film, where the velocity of the Rayleigh wave is dependent on elastic properties and densities of both the film and the substrate, and is also dependent on the thickness of the film, said data processor further operates to measure frequency of oscillations in $\Delta R(t)$ to obtain the Rayleigh wave velocity $c_R$; to detect a component of the strain pulses that propagates through the thickness of the film and that is reflected back at the interface with the substrate, thereby giving a sharp feature in $\Delta R(t)$ at a time $2w/c_L$; and, using the determined Rayleigh wave velocity $c_R$ and a time $\tau_L$ equal to $2w/c_L$, where $c_L$ is the longitudinal sound velocity, to determine the longitudinal and transverse sound velocity and the thickness of the film.

30. A system as in claim 22, wherein at least one of the pump pulses and the probe pulses are directed through said mask by said optical system at normal incidence to the free surface of the film.

31. A system as in claim 22, wherein at least one of the pump pulses and the probe pulses are directed through said mask by said optical system at oblique incidence to the free surface of the film.

32. A system as in claim 22, wherein the sample comprises features that are laterally patterned.

33. A system as in claim 22, wherein the sample includes at least one region that is implanted during an ion implant process, wherein said pump pulses being spatially distributed by said at least one grating generate a spatially distributed density of electrons and holes within the sample, said spatially distributed density of electrons and holes causing a change in optical constants of the sample, and wherein the determined at least one characteristic of the sample is related to at least one of (A) a number of ions implanted per unit area of the surface of the sample; (B) a kinetic energy of the ions that are directed at the surface of the sample; (C) a direction at which the ion beam is incident onto the surface of the sample; (D) an ion current per unit area during the ion implant process; (E) the species of the implanted ion; (F) the charge on the implanted ion; (G) a duration of time that the ion-implanted sample is annealed; and (H) a temperature at which the ion-implanted sample is annealed.

34. A mask adapted to be placed over a free surface of a film to be characterized, said mask being transparent and having a top surface and a bottom surface that is placed adjacent to the free surface of the film, the bottom surface of said mask comprising a plurality of features forming at least one grating for spatially distributing optical pump pulses so as to launch a plurality of spatially distributed strain pulses within the film, the strain pulses causing a change in optical constants of the film, said at least one grating further for spatially distributing optical probe pulses individual ones of which are applied after an individual one of the optical pump pulses.

35. A mask as in claim 34, wherein features of said grating are spaced apart by an amount that is a function of a thickness of the film.

36. A mask as in claim 34, wherein features of said grating form a one dimensional or a two dimensional array of features.

37. A mask as in claim 34, wherein features of said grating are etched into said bottom surface.

38. A mask as in claim 34, wherein features of said grating are formed upon said bottom surface.

39. A mask as in claim 34, wherein said mask has a non-uniform thickness such that features of said grating are at least partially surrounded by an area of said bottom surface that is not coplanar with said features.

40. A method for determining the electrical resistivity of a film that comprises part of a sample having an underlying substrate, comprising steps of:
 (A) placing a mask over a free surface of the film, the mask having a top surface and a bottom surface that is placed adjacent to the free surface of the film, the bottom surface of the mask comprising a plurality of features having a known feature repeat distance w;
 (B) directing optical pump pulses through the mask to the free surface of the film, individual ones of the pump pulses being followed by at least one optical probe pulse, said pump pulses being spatially distributed by said at least one grating for spatially varying the temperature within the film and causing a causing a change in optical constants of the film;
 (C) detecting a reflected or transmitted portion of said probe pulses, said probe pulses also being spatially distributed by said at least one grating;
 (D) measuring $\Delta R(t)$ as a function of a time t after the application of the pump pulses using the mask of known repeat distance w;
 (E) assuming values for the thermal conductivity $\kappa_{film}$ of the film, the thermal conductivity $\kappa_{sub}$ of the substrate, and the Kapitza conductance $\sigma_K$ between the film and the substrate;
 (F) calculating an initial temperature distribution within the film;
 (G) calculating the temperature distribution within the film at later times based on the assumed values for the thermal conductivity of the film, the thermal conductivity of the substrate, and the Kapitza conductance between the film and the substrate;
 (H) calculating an expected change in reflectivity $\Delta R(t)$ based on the calculated temperature distribution;
 (I) adjusting the parameters $\kappa_{film}$, $\kappa_{sub}$, and $\sigma_K$, and repeating Steps (F)–(H) so as to obtain a best fit to the measured $\Delta R(t)$; and
 (J) calculating the electrical resistivity from the thermal conductivity.

41. A method for determining at least one characteristic of a sample comprising a substrate and at least one film disposed on or over a surface of the substrate, the sample further comprising at least one region that is implanted during an ion implant process, comprising steps of:
 placing a mask over a free surface of the at least one film, the mask having a top surface and a bottom surface that is placed adjacent to the free surface of the film, the bottom surface of the mask comprising a plurality of features forming at least one grating;
 directing optical pump pulses through the mask to the free surface of the film, individual ones of the pump pulses being followed by at least one optical probe pulse, said pump pulses being spatially distributed by said at least one grating for generating a spatially distributed density of electrons and holes within the sample, said spatially distributed density of electrons and holes causing a change in optical constants of the sample;
 detecting a reflected or transmitted portion of said probe pulses, said probe pulses also being spatially distributed by said at least one grating;
 measuring a change in at least one characteristic of at least one of reflected or transmitted probe pulses due to the change in optical constants; and
 determining at least one characteristic of the ion implanted region from the measured change in the at least one characteristic of the probe pulses.

42. A method as in claim 41, wherein the determined at least one characteristic is related to a number of ions implanted per unit area of the surface of the sample.

43. A method as in claim 41, wherein the determined at least one characteristic is related to a kinetic energy of the ions that are directed at the surface of the sample.

44. A method as in claim 41, wherein the determined at least one characteristic is related to a direction at which an ion beam is incident onto the surface of the sample.

45. A method as in claim 41, wherein the determined at least one characteristic is related to an ion current per unit area during the ion implant process.

46. A method as in claim 41, wherein the determined at least one characteristic is related to the species of the implanted ion.

47. A method as in claim 41, wherein the determined at least one characteristic is related to the charge on the implanted ion.

48. A method as in claim 41, wherein the determined at least one characteristic is related to a duration of time that the ion-implanted sample is annealed.

49. A method as in claim 41, wherein the determined at least one characteristic is related to a temperature at which the ion-implanted sample is annealed.

50. A system for determining at least one characteristic of a sample comprising a substrate and at least one film disposed on or over a surface of the substrate, the sample comprising at least one region that is implanted during an ion implant process, comprising:

a mask adapted for being placed over a free surface of the at least one film, the mask having a top surface and a bottom surface that is placed adjacent to the free surface of the film, the bottom surface of the mask comprising a plurality of features forming at least one grating;

an optical system for directing optical pump pulses through the mask to the free surface of the film, individual ones of the pump pulses being followed by at least one optical probe pulse, said pump pulses being spatially distributed by said at least one grating for generating a spatially distributed density of electrons and holes within the sample, said spatially distributed density of electrons and holes causing a change in optical constants of the sample;

an optical detector for detecting a reflected or transmitted portion of said probe pulses, said probe pulses also being spatially distributed by said at least one grating; and a data processor for measuring a change in at least one characteristic of at least one of reflected or transmitted probe pulses due to the change in optical constants and for determining at least one characteristic of the ion implanted region from the measured change in the at least one characteristic of the probe pulses.

51. A system as in claim 50, wherein the determined at least one characteristic is related to at least one of (A) a number of ions implanted per unit area of the surface of the sample; (B) a kinetic energy of the ions that are directed at the surface of the sample; (C) a direction at which the ion beam is incident onto the surface of the sample; (D) an ion current per unit area during the ion implant process; (E) the species of the implanted ion; (F) the charge on the implanted ion; (G) a duration of time that the ion-implanted sample is annealed; and (H) a temperature at which the ion-implanted sample is annealed.

52. A method for determining at least one characteristic of a sample comprising a substrate and at least one film disposed on or over a surface of the substrate, comprising steps of:

placing a mask over a free surface of the at least one film, the mask having a top surface and a bottom surface that is placed adjacent to the free surface of the film, the bottom surface of the mask comprising a plurality of features forming at least one grating;

directing optical pump pulses through the mask to the free surface of the film, individual ones of the pump pulses being followed by at least one optical probe pulse, said pump pulses being spatially distributed by said at least one grating for generating a spatially distributed variation in temperature in the film, said spatially distributed variation in temperature causing a change in optical constants of the film;

detecting a reflected or transmitted portion of said probe pulses, said probe pulses also being spatially distributed by said at least one grating;

measuring a change in at least one characteristic of at least one of reflected or transmitted probe pulses due to the change in optical constants; and determining the at least one characteristic of the sample from the measured change in the at least one characteristic of the probe pulses.

* * * * *

UNITED STATES PATENT AND TRADEMARK OFFICE
CERTIFICATE OF CORRECTION

PATENT NO.    : 6,381,019 B1  
DATED         : April 30, 2002  
INVENTOR(S)   : Humphrey J. Maris It is certified that error appears in the above-identified patent and that said Letters Patent is hereby corrected as shown below:

Column 7,  
Line 31, after "equal to" delete "$2w/c_L$" and insert -- $2d/c_L$ --  
Line 52, after "at a time" delete "$2w/c_L$" and insert -- $2d/c_L$ --

Column 10,  
Line 19, after "is a constant" delete "$K=2\pi n/w$" and insert -- $k=2\pi/w$ --  
Line 49, after "to the average" delete "_"

Column 11,  
Line 9, after "of time" delete "_"  
Line 22, after "$K_{film}\Delta T$, where" delete "Kfilm" and insert -- $K_{film}$ --

Column 14,  
Line 65, after "equal to" delete "$2w/c_L$" and insert -- $2d/c_L$ --

Column 15,  
Line 12, after "at a time" delete "$2w/c_L$" and insert -- $2d/c_L$ --  
Line 14, after "equal to" delete "$2w/c_L$" and insert -- $2d/c_L$ --

Column 16,  
Line 35, after "equal to" delete "$2w/c_L$" and insert -- $2d/c_L$ --  
Line 48, delete "$2/c_L$" and insert -- $2d/c_L$ --  
Line 49, after "equal to" delete "$2w/c_L$" and insert -- $2d/c_L$ --

Signed and Sealed this

Third Day of June, 2003

JAMES E. ROGAN  
*Director of the United States Patent and Trademark Office*